US012260652B2

(12) United States Patent
Brohl et al.

(10) Patent No.: US 12,260,652 B2
(45) Date of Patent: Mar. 25, 2025

(54) SYSTEM AND METHOD FOR DETERMINING EVENTS IN A CABIN OF A VEHICLE

(71) Applicant: Robert Bosch GmbH, Stuttgart (DE)

(72) Inventors: Steven Ralf Brohl, Roseville, MI (US); Russell Watts, Holt, MI (US); Philip Ventimiglia, Northville, MI (US)

(73) Assignee: Robert Bosch GmbH, Stuttgart (DE)

( * ) Notice: Subject to any disclaimer, the term of this patent is extended or adjusted under 35 U.S.C. 154(b) by 114 days.

(21) Appl. No.: 18/173,222

(22) Filed: Feb. 23, 2023

(65) Prior Publication Data
US 2024/0290111 A1    Aug. 29, 2024

(51) Int. Cl.
| | |
|---|---|
| *G06V 20/59* | (2022.01) |
| *G01N 33/00* | (2006.01) |
| *G06V 10/774* | (2022.01) |
| *G06V 10/82* | (2022.01) |
| *H04N 7/18* | (2006.01) |

(52) U.S. Cl.
CPC ......... *G06V 20/59* (2022.01); *G01N 33/0062* (2013.01); *G06V 10/774* (2022.01); *G06V 10/82* (2022.01); *H04N 7/183* (2013.01); *H04N 7/188* (2013.01); *G01N 33/0068* (2024.05)

(58) Field of Classification Search
None
See application file for complete search history.

(56) References Cited

U.S. PATENT DOCUMENTS

| | | | |
|---|---|---|---|
| 10,688,961 B2 | 6/2020 | Oesterling et al. | |
| 10,776,643 B1 | 9/2020 | Meister et al. | |
| 11,104,227 B2 | 8/2021 | Hök et al. | |
| 11,334,985 B2 | 5/2022 | Ventimiglia | |
| 2021/0188051 A1 | 6/2021 | Macneille et al. | |
| 2021/0190516 A1 | 6/2021 | Ventimiglia et al. | |
| 2021/0310939 A1 | 10/2021 | Brauer et al. | |
| 2022/0055440 A1 | 2/2022 | Varughese et al. | |
| 2022/0058930 A1 | 2/2022 | Varughese et al. | |
| 2023/0288770 A1* | 9/2023 | Gupta | H02J 50/20 |

\* cited by examiner

*Primary Examiner* — Christopher G Findley
(74) *Attorney, Agent, or Firm* — Maginot, Moore & Beck LLP

(57) ABSTRACT

A system for determining an event in a cabin of a vehicle includes a gas sensor, a PM sensor, an image sensor configured to generate an image signal corresponding to a captured image of at least a portion of the cabin, and a controller operably connected to the gas, PM, and image sensors. The controller is configured to receive the sensor signals, generate time series datasets of the sensor signals, determine an event in the cabin of the vehicle by analyzing the time series datasets using a machine learning model, and in response to determining the event in the cabin, operate the image sensor to generate image data corresponding to a captured image of at least a portion of the cabin of the vehicle.

20 Claims, 8 Drawing Sheets

SYSTEM AND METHOD FOR DETERMINING EVENTS IN A CABIN OF A VEHICLE

CROSS-REFERENCE TO RELATED APPLICATION

This application is related to U.S. patent application Ser. No. 18/173,216, filed on even date herewith, the disclosure of which is incorporated herein by reference in its entirety.

FIELD

The system and method disclosed herein relates to vehicle cabin monitoring and, more particularly, to a system for determining events in a vehicle cabin.

BACKGROUND

Unless otherwise indicated herein, the materials described in this section are not prior art to the claims in this application and are not admitted to the prior art by inclusion in this section.

In shared vehicle services, such as ride sharing services, taxi services, and car rental services, shared vehicles are often driven by drivers or ridden in by passengers who are not the owner of the vehicle. A common problem with such services is that customers can be careless about how they treat the vehicle during their short time as a passenger or driver. In light of this, operators of such services often put in place various rules or policies regarding how the vehicle should be treated by the customer. However, modern incarnations of these services are technology driven and often entirely autonomous, so as to require little or no direct interaction with the owner of the vehicle or the operator of the service. As a result, effective enforcement of these rules or policies can be challenging and sometimes cost-prohibitive. Accordingly, it would be beneficial to provide a system that enables autonomous detection and classifying of events within the vehicle that reduces the need for human intervention in enforcing rules or policies, as well as remedying violations.

SUMMARY

In one embodiment, a system for determining an event in a cabin of a vehicle includes a gas sensor configured to generate a first sensor signal associated with a quantity of at least one gas or volatile organic compound (VOC) in ambient air of the cabin, a particulate matter (PM) sensor configured to generate a second sensor signal associated with a quantity of particulate matter in the ambient air of the cabin, an image sensor configured to generate an image signal corresponding to a captured image of at least a portion of the cabin of the vehicle, and a controller operably connected to the gas sensor and the PM sensor. The controller is configured to receive the first and second sensor signals from the gas sensor and the PM sensor and generate a first time series dataset of the first sensor signals and a corresponding second time series dataset of the second sensor signals. In addition, the controller is further configured to determine an event in the cabin of the vehicle by analyzing both the first and second time series datasets using a machine learning model that has been trained with training data corresponding to time series data of PM readings and gas sensor readings of known events and, in response to determining the event in the cabin, operate the image sensor to generate image data corresponding to a captured image of at least a portion of the cabin of the vehicle.

The controller may be, in various embodiments, further configured to notify an operator of the vehicle of the determined event.

In at least one embodiment, the notifying of the operator of the vehicle includes transmitting to the operator the captured image of at least the portion of the cabin of the vehicle.

In some embodiments, the notifying of the operator further includes transmitting to the operator at least part of the first and second time series datasets associated with the determined event The system may further include a memory operably connected to the controller, and the controller may be further configured to store at least part of the first and second time series datasets and the image of at least the portion of the cabin of the vehicle in the memory in such a way that the at least part of the first and second time series datasets and the image are associated with the determined event.

In some embodiments, the machine learning model or a further machine learning model has been trained is training data corresponding to captured images of the known events, and the controller is further configured to confirm the determined event by using the machine learning model or the further machine learning model to analyze the image of the at least the portion of the cabin of the vehicle.

In one or more embodiments, the machine learning model is an artificial neural network in some embodiments.

In further embodiments, the controller is further configured to compare one of the first sensor signal and the second sensor signal with a threshold value before generating the first and second time series datasets, and generate the first and second time series datasets and determine the event in the cabin in response to the one of the first sensor signal and the second sensor signal exceeding the threshold value.

In at least one embodiment, the controller includes at least one local processor disposed in the vehicle and at least one remote processor disposed remote from the vehicle and in wireless communication with the at least one local processor. The at least one local processor is configured to compare the one of the first sensor signal and the second sensor signal with the threshold value, and the at least one remote processor is configured to determine the event in the cabin of the vehicle.

Additionally, in another embodiment, the controller is further configured to update the training data to include the first and second datasets in response to determining the event.

In a further embodiment, a method for determining an event in a cabin of a vehicle includes receiving, with a controller, a first sensor signal from a gas sensor configured to generate the first sensor signal, which is associated with a quantity of at least one gas or volatile organic compound (VOC) in ambient air of the cabin and receiving, with the controller, a second sensor signal from a particulate matter (PM) sensor configured to generate the second signal, which is associated with a quantity of particulate matter in the ambient air of the cabin. The method further includes generating, with the controller, a first time series dataset of the first sensor signals and a corresponding second time series dataset of the second sensor signals and determining, with the controller, an event in the cabin of the vehicle by analyzing both the first and second time series datasets using a machine learning model that has been trained with training data corresponding to time series data of PM readings and gas sensor readings of known events. In response to determining the event in the cabin, the method includes operating the image sensor to generate image data corresponding to a captured image of at least a portion of the cabin of the vehicle.

BRIEF DESCRIPTION OF THE DRAWINGS

The foregoing aspects and other features of an in-vehicle sensing system are explained in the following description, taken in connection with the accompanying drawings.

DETAILED DESCRIPTION

Figure 1:
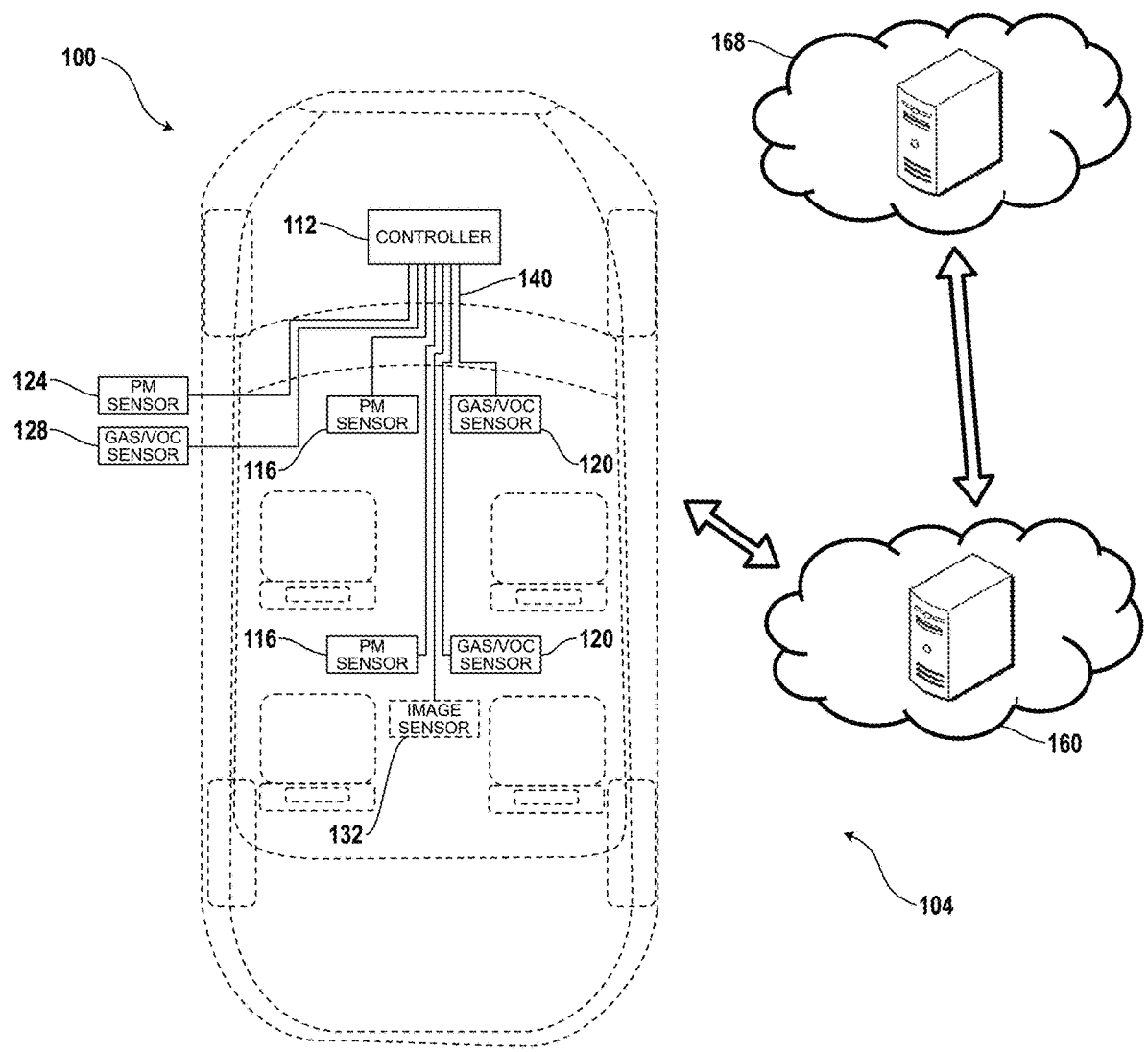
FIG. 1 shows a schematic view of a vehicle having a cabin event detection system according to the disclosure.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles of the disclosure as would normally occur to one skilled in the art which this disclosure pertains.

System Overview

FIG. 1 shows a simplified schematic diagram of a vehicle 100 having a cabin event detection system 104 for monitoring at least a cabin 108 (also referred to as a passenger space) of a vehicle 100. The cabin event detection system 104 is advantageous for use in the context of a shared vehicle service in which the shared vehicle 100 is driven by drivers or ridden in by passengers who are not the owner of the shared vehicle 100. Such shared vehicle services might include, but are not limited to, a car rental service, an autonomous taxi service, or a ride sharing service. In many such shared vehicle services, a customer may engage the services of the shared vehicle service in an automated manner using a smartphone application, a website, an on-site kiosk, or the like, which involves little or no direct human intervention by the operator of the shared vehicle service. The reader should appreciate that reference to the "operator" herein can include, without limitation, the vehicle owner or a person or entity that manages the shared vehicle service and that may or may not be, in a strict sense, the owner of the vehicle.

The cabin event detection system 104 advantageously enables operators of a shared vehicle to monitor the condition of the vehicle 100, enforce rules and policies, and provide additional benefits to the customer with minimal human intervention. Such rules and policies might include rules against smoking, vaping, or using illicit or illegal drugs in the vehicle 100, rules against consuming or possessing alcohol in the vehicle, driving or using the vehicle 100 under the influence of alcohol, rules against eating or drinking in the vehicle 100, rules against transporting pets in the vehicle 100, or policies prohibiting dirtying the vehicle by, for example, bodily fluids (such as vomit, urine, blood, or feces), excessive perfume, or introducing other potentially objectionable odors into the cabin. The rules and policies of the vehicle operator may include billing the user for cleaning of the vehicle 100 after usage by the customer if the user violates one or more of the rules or policies, and/or terminating or suspending the user's permission to use the operator's vehicles after the user violates the rules or policies a specified number of times.

The cabin event detection system 104 is configured to detect and classify events occurring in at least the cabin 108. As used here, the term "event" refers to occurrences in the cabin 108 that may negatively affect the enjoyability of another user to use the vehicle, or that may cause or indicate a danger to current or future users of the vehicle 100. These events can be broadly classified into smoking events, vaping events, alcohol events, cleanliness events, and emergency events. Smoking events include combustion-related events such as tobacco smoking (including cigarette, cigar, and pipe smoking), marijuana smoking, smoking of illegal or illicit drugs, burning of incense, etc. Vaping events include, for example, e-cigarette events, e-vapor product events, or heated tobacco product (such as IQOS) events. Alcohol events may include the presence of alcohol/ethanol in a driver or passenger's breath, or presence of open containers of alcohol in the cabin 108 of the vehicle 100. Cleanliness events may include, for example, the presence or spills of food and/or drinks, perfumes, pet or animal odors, excessive dust in the cabin 108, or the presence of bodily fluids such as vomit, urine, feces, or blood. Emergency events may include, for example, smoke or fire in the vehicle 100 not associated with a smoking event, airbag deployment, presence of gasoline or other potentially dangerous compounds in the cabin 108, elevated levels of carbon monoxide in the cabin 108, or elevated levels of other chemicals or toxins in the cabin 108 that could pose a danger to the occupants of the vehicle 100.

Figure 2:
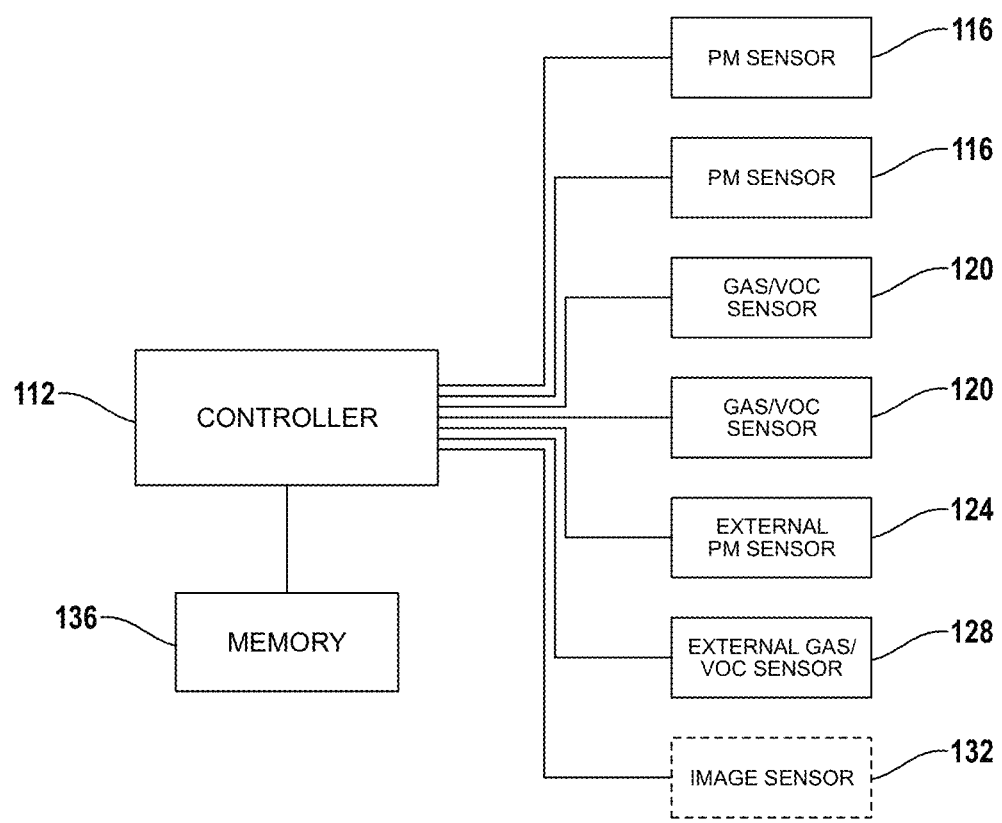
FIG. 2 shows a simplified block diagram of the cabin event detection system of FIG. 1.

With continuing reference to FIG. 1 and further reference to FIG. 2, the cabin event detection system 104 includes a controller 112, at least one particulate matter (PM) sensor 116 and at least one gas/VOC sensor 120. The reader should appreciate that while the embodiment illustrated in FIG. 1 depicts two PM sensors 116 and two gas/VOC sensors 120, the cabin event detection system 104 may include any desired number of PM sensors and any desired number of gas/VOC sensors. The PM sensors 116 and gas/VOC sensors 120 are configured to detect particulate matter and gas/VOCs, respectively, present in the cabin 108. As such, the PM sensors 116 and gas/VOC sensors 120 may be arranged directly in the cabin 108 or arranged such that air from the cabin 108 is received by the PM sensors 116 and gas/VOC sensors 120. By way of example, PM and gas/VOC sensors 116, 120 may be attached to the windshield or windows, integrated in or attached to the vehicle roof, integrated in the headliner, integrated in or attached to the vehicle seats or dashboard, integrated in or attached to the ducts of the heating and air conditioning system, any other suitable location, or any combination of the aforementioned locations. Additionally, the PM sensors 116 and the gas/VOC sensors 120 may be distributed through the cabin 108 to enable detection of particulate matter and gases/VOCs at different locations within the cabin 108.

The PM sensors 116 may any desired particulate matter concentration sensor or combination of sensors which can provide signals related to an airborne particulate matter concentration. In one embodiment, one or more of the PM sensors is a sensor utilizing an LED in combination with a photodiode. Preferably the airborne PM sensors 116 can detect and distinguish between particulate matter with particle diameter up to one micron (PM1), and/or 2.5 microns (PM2.5), and/or 4 microns (PM4), and/or 10 microns (PM10). In some embodiments, however, the airborne PM concentration sensors may not distinguish between particles of different diameters. For example, in some embodiments a PM2.5 sensor provides an output related to the particulate matter concentration of particulate matter of up to 2.5 microns.

The gas/VOC sensors 120 may be any suitable type of gas/VOC sensor such as, for example, catalytic, electrochemical, chemFET, resonant, metal oxide semiconductor (MOx), infrared (IR), chromatography, photoionization, chemi-luminescence, etc. In one particular embodiment, the gas/VOC sensors 120 are metal oxide sensors. Metal oxide gas/VOC sensors heat VOCs in the form of gas (such as alcohol/ethanol vapor) or smoke (such as cigarette smoke), which causes a chemical reaction that converts the organic gases to $CO_2$ and water. The chemical reactions consume oxygen, which results in a lower oxygen level near the sensing element, and thereby a reduction in gas resistance (R) that is measured and converted to the sensor signal. Alternatively, the gas/VOC sensor may output the gas conductivity as the sensor signal, which is the inverse of resistance (i.e. 1/R).

In some embodiments, the cabin event detection system 104 further includes at least one external PM sensor 124 and/or at least one external gas/VOC sensor 128 configured to sense the particulate matter and gas/VOCs, respectively, outside the vehicle 100. The external sensors 124, 128 enable the cabin event detection system 104 to identify or omit detection of events caused by PM or gases outside the vehicle 100 to reduce false positives in the detection of cabin events.

Additionally, in some embodiments, the cabin event detection system 104 includes at least one image sensor 132, for example a camera, configured to capture images of at least one area in the cabin 108 of the vehicle 100. The image sensor 132 may include, for example, a CCD (charge coupled device) or a CMOS (complementary metal-oxide-semiconductor) configured to capture images in optical and/or infrared wavelengths. In one embodiment, a single image sensor is arranged at the front of the vehicle, for example on the windshield, and oriented so as to capture an image of the entire cabin 108. In another embodiment, multiple image sensors are arranged in the cabin 108 so as to provide images that cover most or all of the cabin 108 of the vehicle 100.

The controller 112 of the cabin event detection system 104 is operably connected to the sensors 116-132 wirelessly, using wired connections, or using a combination of wired and wireless connections. In one embodiment, the controller 112 is connected to the sensors 116-132 via one or more communication buses 140. The communication buses 140 may, for example, take the form of one or more I2C (Inter-Integrated Circuit) buses, I2S (Inter-IC Sound) buses, USB (Universal Serial Bus) buses, and/or CAN (Controller Area Network) buses. Accordingly, the controller 112 may include suitable bus controllers for communicating with the sensors via the communication buses.

The controller 112 is configured to receive sensor data from the sensors 116-132 corresponding to the sensor signals and/or image data generated by the sensors 116-132. The sensor data may be provided by the sensors 116-132 and/or accessed by the controller 112 at a predetermined rate (e.g., once per second).

The controller 112 is implemented in various embodiments with one or more general or specialized programmable processors that execute programmed instructions which are stored in a memory 136. In some embodiments at least some of the functionality of the controller 112 is provided by a vehicular control system and/or remotely from the vehicle 100 such as by a remote controller located at a vehicle fleet management center, a service center, a manufacturing center, etc. Thus, in some embodiments, the controller 112 is embodied as multiple controllers/processors which are located locally in the vehicle 100 and/or remotely from the vehicle 100 (e.g. at the cloud-storage backend 160).

The program instructions and data required to perform the programmed functions described herein are stored in the memory 136. In some embodiments, the memory 136 is embodied as a plurality of memories which in some embodiments include one or more memories remote from the vehicle 100. The processors, the memory, and interface circuitry components in various embodiments are provided on a printed circuit card or provided as a circuit in an application specific integrated circuit (ASIC). In some embodiments, the circuits are implemented with discrete components or circuits provided in VLSI circuits. The circuits described herein are also implemented in some embodiments with a combination of processors, ASICs, discrete components, or VLSI circuits.

The cabin event detection system 104 is configured to monitor the ambient air inside the cabin 108 of the vehicle 100 to detect events occurring in the cabin 108. Particularly, the cabin event detection system 104 is configured to process sensor data received from the sensors 116-132 to infer and classify one or more smoking events, vaping events, alcohol events, cleanliness events, or emergency events occurring in the cabin 108 of the vehicle 100. The cabin event detection system 104 utilizes appropriate algorithms, models (e.g., machine learning models such as artificial neural networks), or thresholds to interpret the sensor data and enrich the data with metadata and event detection and classification. It will be appreciated by those of ordinary skill in the art that the term "metadata" refers to any data that describes or gives information about other data (e.g., the sensor data).

The cabin event detection system 104 is configured to upload, by a cellular Internet connection, relevant sensor data, event data, or other metadata to a cloud storage backend 160 for storage thereat. The data uploaded to the cloud storage backend 160 is, in some embodiments, accessible by a third-party cloud backend 168. The third-party backend 168 is, for example, associated with the shared vehicle service discussed above, such as a car rental service, an autonomous taxi service, or a ride sharing service. In this way, an operator of the shared vehicle service can monitor the condition of the shared vehicle 100, enforce rules and policies, and provide additional benefits to the customer with minimal human intervention.

Event Classification and Determination

The cabin event detection system 104 is configured to detect and classify one or more events occurring in the cabin 108 of the vehicle 100 based on sensor data received from at least one PM sensor 116 and at least one gas/VOC sensor 120. In one embodiment, the cabin event detection system 104 executes an event determination algorithm to monitor a curve of particulate matter concentrations and conductance or resistance detected by the PM sensor(s) 116 and the gas/VOC sensor(s) 120, respectively, over time and compares the monitored particulate matter concentrations and conductance/resistance to reference data.

Figure 3:
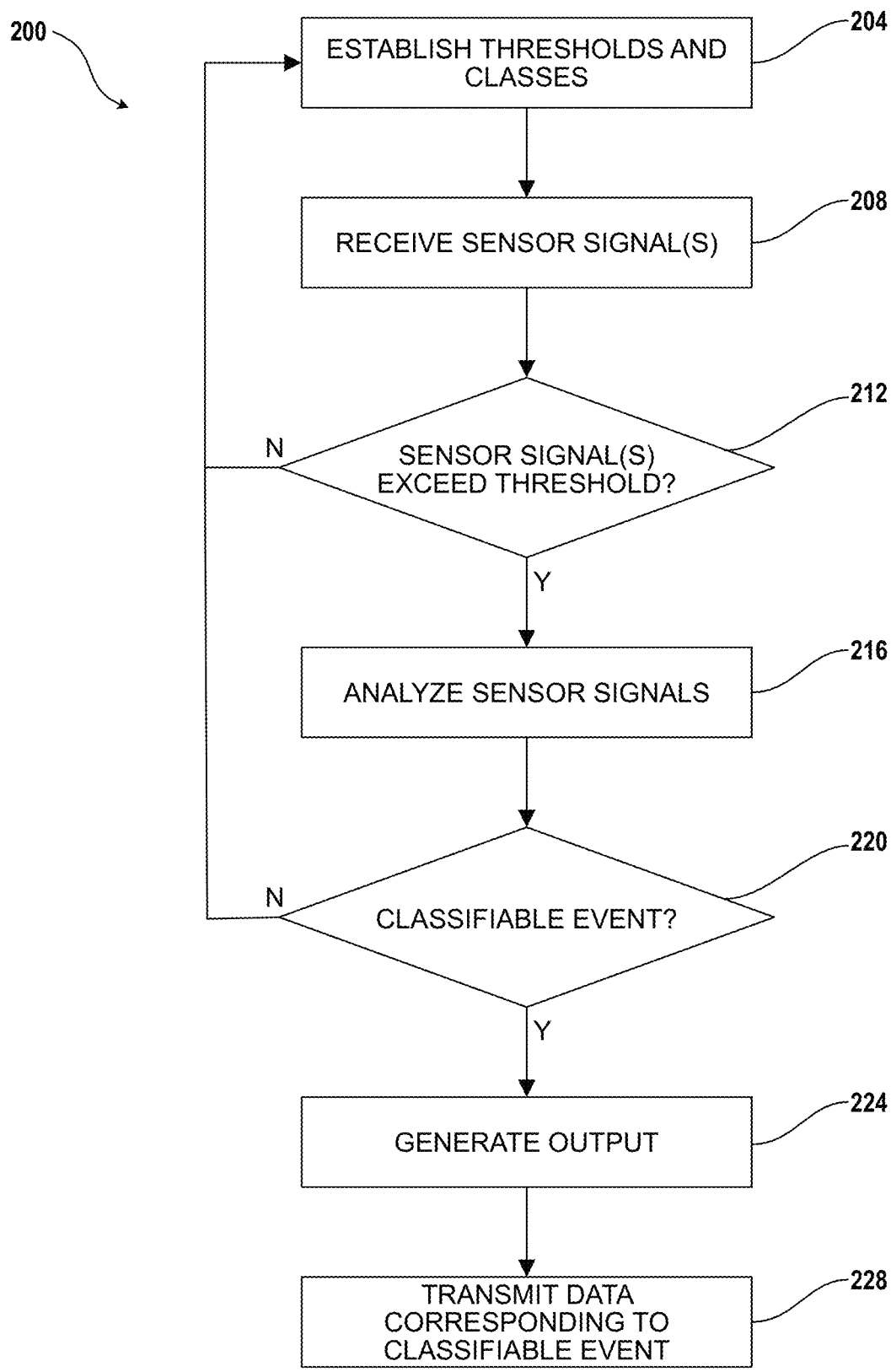
FIG. 3 is a process diagram illustrating a method of operating the cabin event detection system of FIG. 1.

FIG. 3 depicts a method 200 for operating the cabin event detection system 104 to determine (i.e. to detect and classify) an event in the cabin 108 of the vehicle 100. The method 200 is executed at least in part by the controller 112 executing program instructions stored in the memory 136 to detect and determine an event in the cabin 108.

The method 200 begins with establishing one or more threshold values and event classes (block 204). The threshold values may be upper limit or lower limit values of the sensor signals above which or below which, respectively, indicate that a classifiable event has potentially occurred. In some embodiments, the threshold values may be established dynamically based on recent sensor readings. In particular, the controller 112 may obtain previous sensor readings for a specified period of time to establish a baseline sensor signal level, and the threshold value may be established based on the baseline sensor signal level. Alternatively, the threshold values may be predetermined values that are programmed in the memory 136.

Additionally, in some embodiments, the controller 112 may obtain the signal from the external PM sensor 124 and/or the external gas/VOC sensor 128 (collectively the external sensors) to identify the particulate matter and/or gas/VOC concentration of the environment surrounding the vehicle and apply an offset or correction to the threshold value, which is then stored in the memory 136. The offset or correction may be updated periodically based on the signals from the external sensors 124, 128. As a result, high background PM or gas/VOC readings caused by, for example, smog, temperature inversions, external fires, etc., can be accounted for. Accordingly, using the external sensors 124, 128 enables reduction in spurious event detection by differentiating between airborne PM and gas/VOCs introduced from outside of the vehicle and PM and gas/VOCs introduced from within the vehicle.

The classes determined by the cabin event detection system 104 are established based on training data and, in some embodiments, previously received sensor data, collectively referred to as the data. The training data include PM data and gas/VOC data for various known classification events. For example, the training data may include the corresponding PM and gas/VOC sensor data associated with a plurality of known vaping, IQOS, cigar, cigarette, vomit, alcohol, perfume, marijuana, drug, food, pet, etc. events. In particular, the training data is based on time series datasets of the known events for both the PM sensor readings and gas/VOC sensor readings.

The event classification is performed by a machine learning or statistical model that is configured to abstract the sensor data such that it is easier for the cabin event detection system 104 to process. Any desired machine learning or statistical models can be adopted for this purpose, such as clustering (e.g., mean shift, k-means), function approximation (e.g., Gaussian mixture model, neural networks), or simple statistical analysis (e.g., mean and deviation, histogram).

In some embodiments, the model(s) may comprise machine learning models such as nearest neighbor, naive Bayes, decision trees, linear regression, neural networks (including convolution neural networks, recurrent neural networks, or artificial neural networks), or the like. More specifically, as used herein, the term "machine learning model" refers to a system or set of program instructions and/or data configured to implement an algorithm, process, or mathematical model (e.g., a neural network) that predicts or otherwise provides a desired output based on a given input. It will be appreciated that, in general, many or most parameters of a machine learning model are not explicitly programmed and the machine learning model is not, in the traditional sense, explicitly designed to follow particular programmatic rules in order to provide the desired output for a given input. Instead, a machine learning model is provided with a corpus of training data from which it identifies or "learns" implicit patterns and statistical relationships in the data, which are generalized to make predictions or otherwise provide outputs with respect to new data inputs. The result of the training process is embodied in a plurality of learned parameters, kernel weights, and/or filter values that are used in the various components of the machine learning model to perform various operations or functions. To these ends, the processor 112 trains or generates a model representing at least some of the sensor data received from the sensors 116-132 that correspond to a classified event.

In some embodiments, a model is generated that summarizes one or more types of sensor data. Particularly, in one embodiment, the processor 112 trains or generates a model that indicates one or more attributes of time series datasets of the sensor data and the associated event classification. Specifically, the model indicates a mathematical function that fits to and, thus estimates, a classification of an event based on the PM and gas/VOC sensor data.

Figure 4:
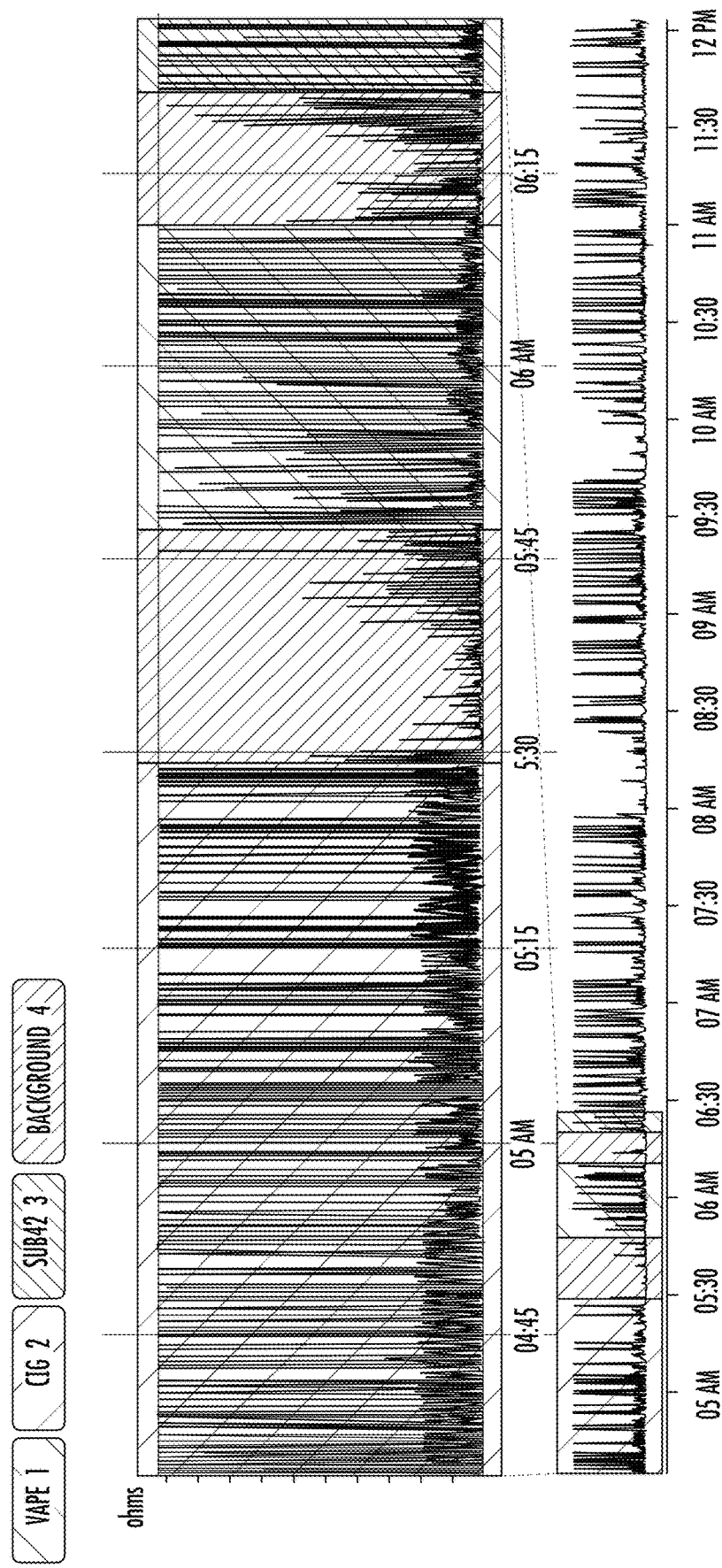
FIG. 4 shows an exemplary set of training data used to train a cabin event detection such as the system of FIG. 1 in graphical form.

FIG. 4, for example, illustrates a set of training data in which the gas/VOC sensor resistance signals are labeled at specific times that correspond to certain events such as vaping events, cigarette smoking events, and background signals (i.e. no classifiable event). The PM sensor signals, which correspond to PM1, PM4, and PM10 data, corresponding to the same time are input into the machine learning model with the gas/VOC sensor resistance data to form a corpus of training data for the machine learning model. The machine learning model, for example an artificial neural network, analyzes the PM and gas/VOC sensor data and generates a mathematical model that classifies known events in the training data based on both the PM sensor data and the gas/VOC sensor data.

Referring back to FIG. 3, after the thresholds and classes are established, the method 200 continues with receiving the sensor signals from at least the internal PM and gas/VOC sensors 116, 120, and optionally the signals from the external PM and/or gas/VOC signals 124, 128, and/or the signals from the image sensor 132 (block 208).

Once the signals are received, the controller 112 evaluates whether the sensor signals exceed the threshold (block 212). Specifically, as used herein, reference to the sensor signals "exceeding" the threshold can refer to the sensor signals being above an upper threshold or below a lower threshold, depending on the type of sensor reading. For instance, the gas resistance has a lower threshold below which a classifiable event may have occurred, while gas conductance and PM have an upper threshold above which a classifiable event may have occurred. In some embodiments, the evaluation is only performed on the sensor signals from one sensor, while in other embodiments the evaluation is performed on all sensors of a given type (e.g. all PM sensors 116 or all gas/VOC sensors 120). In other embodiments, only one of the sensor readings (e.g. PM1 or PM4 or PM10, or R0 or R1, etc.) for a single sensor, or for all sensors of a given type, is evaluated against the threshold. In this way, the continuous processing required for evaluating sensor signals when the background levels of PM or gas/VOCs are low is reduced compared to continuously evaluating all sensor signals.

Alternatively, in some embodiments, some or all of the sensor readings from each of the sensors are evaluated against a threshold or against independent thresholds, and the determination of whether the signals exceed the threshold is made based on a single sensor reading exceeding its threshold, a minimum number of sensor readings exceeding its respective threshold, a sum or error function (or other arithmetic formula) of the amount by which the various sensor readings exceed their respective thresholds, or in another desired manner.

If the controller 112 determines in block 212 that the sensor signals exceed the threshold, the controller proceeds to analyze the sensor signals (block 216). Specifically, the analysis of the sensor signals includes generating time series datasets of the sensor readings of at least one PM sensor and at least one gas/VOC sensor, and evaluating the time series datasets according to the machine learning model to determine whether the model classifies the received sensor signals of the time series datasets from both the PM sensors 116 and the gas/VOC sensors 120 as one of the events learned in the training process (block 220).

In some embodiments, the analysis of the sensor signals at block 216 and the determination of whether a classifiable event has occurred at block 220 are performed by the controller 112 by a processor located in or on the vehicle 100. Since the analysis is only performed after one or more thresholds are exceeded in block 212, the local processor is not continuously analyzing all the data from every sensor 116-132 in the vehicle 100. Accordingly, the processing power required in the local processor of the vehicle 100 is less than would be required if the sensor signals were constantly analyzed and classified.

Alternatively, in some embodiments, the analysis of the sensor signals at block 216 is performed by a processor of the controller 112 that is located remotely from the vehicle 100, for example in the cloud (e.g. the cloud backend 160). In such an embodiment, the processing capacity required by the remote processor is again reduced compared to an embodiment in which all sensor signals are constantly analyzed. Further, the amount of data transmitted by the controller from the vehicle 100 to the remote processor is reduced since the sensor data is only transmitted after detection of the threshold value being exceeded.

Alternatively, in embodiments in which the remote processor also determines if the threshold value is exceeded, only the sensor data evaluated against the threshold is transmitted until the threshold is exceeded, and the remaining sensor data is not transmitted until after the threshold is determined to be exceeded. Again, the quantity of data transmitted from the vehicle 100 to the cloud backend 160 is less than if the entirety of the sensor data were continuously transmitted to the cloud backend 160.

In one specific embodiment, a local processor of the controller 112 evaluates one or more of the PM sensor signals (e.g. PM1, PM4, and/or PM10) of the PM sensor(s) 116 against the threshold value in block 212. If the threshold is not exceeded, the method continues at block 204 without transmitting sensor data to a remote processor of the controller 112. If, however, the threshold is exceeded (either above an established upper threshold or below an established lower threshold), the local processor of the controller 112 transmits the sensor data, and more specifically time series datasets of the sensor data, from at least the PM sensor(s) 116 and the gas/VOC sensor(s) 120 and, in some embodiments, the external sensors 124, 128 and/or image sensor 132, to the remote processor of the controller 112. The remote processor of the controller 112 then executes the analysis of the sensor signals (block 216) and the determination of whether a classifiable event (block 220) is detected.

In another similar embodiment, the initial determination of whether the sensor signals exceed the threshold value at block 212 is performed by the local processor on one or more of the gas/VOC sensor readings instead of the PM sensor readings, with the remainder of the process executed in the same manner. This embodiment has the advantage that the PM sensors 116 need not be continuously active. PM sensors typically consume a greater amount of electrical power to operate than gas/VOC sensors, and therefore continuously monitoring only the gas/VOC sensors 120 to evaluate against the threshold values reduces the power consumption required by the cabin event detection system 104.

If, in block 220, the received sensor signals from both the PM sensors 116 and the gas/VOC sensors 120 are classified by the machine learning model as one of the events learned in the training process, the method proceeds to generate an output based on the classified event (block 224). In some embodiments the generated output includes data and/or metadata (collectively "data") associated with the classifiable event. The data associated with the event is then stored in the memory 136, which in various embodiments is locally and/or remotely located, and retrieved at a later time. For example, the data in some embodiments is retrieved during a vehicle inspection after use of the vehicle using, e.g., the vehicles onboard diagnostic port which may be wired or wireless. This retrieved data is then used in assessing charges to the user of the vehicle for cleaning of the vehicle.

In embodiments wherein at least a portion of the memory 136 is remote, the data is transmitted from the vehicle using a communications module in the controller 112 to a remote location for storage and/or further action (block 228). For example, the data may be transmitted from the vehicle 100 and stored in the cloud backend 160 or the third-party backend 168. The stored events may be used by the vehicle operator for a variety of purposes. For instance, the stored data enables detailed reports on the overall cleanliness of a vehicle with regard to smell based on the number and types of events detected over a given time period. Moreover, the data enables the vehicle operator to track the overall health of their vehicles, with detailed metrics that provide information as to how vehicles are treated by users in a particular area, how smell and odors affect the depreciation of their vehicles over time, whether certain vehicles (e.g. high-end vehicles) should not be operated in areas where vehicles are commonly treated poorly, etc. Further, the data can be used to simplify the determination of the vehicle operator when a vehicle needs to be taken out of service and cleaned or how to produce a regular cleaning schedule for vehicles based on common usage statistics for a given area. The stored data may also be used in some embodiments to maintain a cleanliness score with respect to odor or smell data for both the specific vehicle and for a particular user. The system 104 may also allow customers to provide feedback relating to the smell and cleanliness of a vehicle, which can be associated with the stored data to improve the confidence of the event determination over time.

Additionally, as part of the transmission of the generated output, the cabin event detection system 104 may be configured to notify the user and/or operator of a rule or policy violation based on the detected event. For example, the controller 112 may transmit a notification to the user's cellular phone or ride-sharing app via cellular telephony, or via the cloud backend 160 or the third-party backend 168. In another embodiment, the controller 112 is configured to notify the operator of the vehicle of the detected event. For instance, the controller 112 may transmit a notification via, for example, email, SMS, an API (application programming interface) connection, or a dedicated user interface (i.e. operator dashboard), to the operator of the vehicle. The notification may include data corresponding to a timestamp of the detected event, a vehicle ID, the event metadata, which may include the raw data from the datasets and/or the datasets presented in a visual manner, i.e. a graphical manner, as evidence of the detected event. The operator then has the ability to view the data corresponding to the determined event and take appropriate action based on the determined event and the corresponding data.

In some embodiments, the controller 112 may be configured to notify a third-party service provider of the determined event and the associated metadata. For example, the controller 112 may transmit a notification via, for example, email, SMS, an API connection, or a dedicated interface (i.e. dashboard) to a cleaning or maintenance service provider to dispatch cleaning or maintenance services to the vehicle 100. In some embodiments, the data and metadata corresponding to a plurality of classifiable events occurring over a predetermined time period is aggregated and transmitted to the third-party service provider, e.g. a fleet operator, at a regular interval to provide information as to the usage of the fleet operator's vehicles.

In conjunction with the rule or policy violation, the cabin event detection system 104, the cloud backend 160 or the third-party backend 168 may be configured to take action against the user based on the detected event. Specifically, the user may be prevented from further using the vehicle. For example, the user may be flagged in a database (e.g. in the cloud backend 160 or the third-party backend 168) such that the vehicle, and other vehicles in the rideshare or self-driving vehicle fleet, no longer accepts ride requests from the user. Alternatively, the user may be assessed a fine for performing a prohibited event by being flagged in the database.

In some embodiments, the method 200 further includes operating the vehicle based on the generated output. For example, in one embodiment, the method includes operating the vehicle's drive system based on the generated output. The operation of the vehicle drive system may include operating the drive system to safely brake, pull over, and/or stop in response to the classified event. The vehicle may also be operated to prevent the vehicle from moving in response to the classified event. In a further embodiment, the vehicle may be operated to continue its normal operation based on the classified event. In still other embodiments, the vehicle is operated to complete the current ride, and then travel to a specified location for cleaning and/or maintenance in response to the generated output.

The operation of the vehicle may also include operating various elements of the vehicle's climate control system, windows, doors, lights, display screen(s) and/or speakers in response to the classified event. For instance, the vehicle may be operated to open the windows and/or activate the climate control system to ventilate the vehicle in response to some classified events, e.g. smoking, vaping, certain cleanliness or emergency events, etc. The vehicle may also be operated to flash the lights inside the vehicle, display an alert or a warning message on the display screen(s), and/or play an alert or warning sound or recorded message using the vehicle speakers to alert the user that the event has been detected.

As will be discussed in more detail below, in some embodiments incorporating the image sensor 132, the operation of the vehicle includes a control signal to operate the image sensor 132 to obtain an image of the cabin 108. The image sensor 132 may be in the form of a plurality of cameras to provide sufficient coverage of the cabin 108 to identify each individual involved in the smoking event. In some embodiments a single image is taken. In other embodiments, a series of images and/or a video is obtained. In some embodiments, an image is obtained each time a classifiable event is identified by the controller 112.

The image may then be transmitted by the controller 112 to the cloud storage backend 160 or the third-party backend 168 for storage and potential further action. Additionally or alternatively, the image may be transmitted along with the notification sent to the user as further evidence of the detected event. The image may also be used as supporting evidence in the event the user disputes the characterization of the classified event as a violation of the rules or policies. Alternatively, the image may be stored in the memory 136 to support the assignment of cleaning charges to one or more passengers in the cabin 108.

Illustrative Examples

Figure 5:
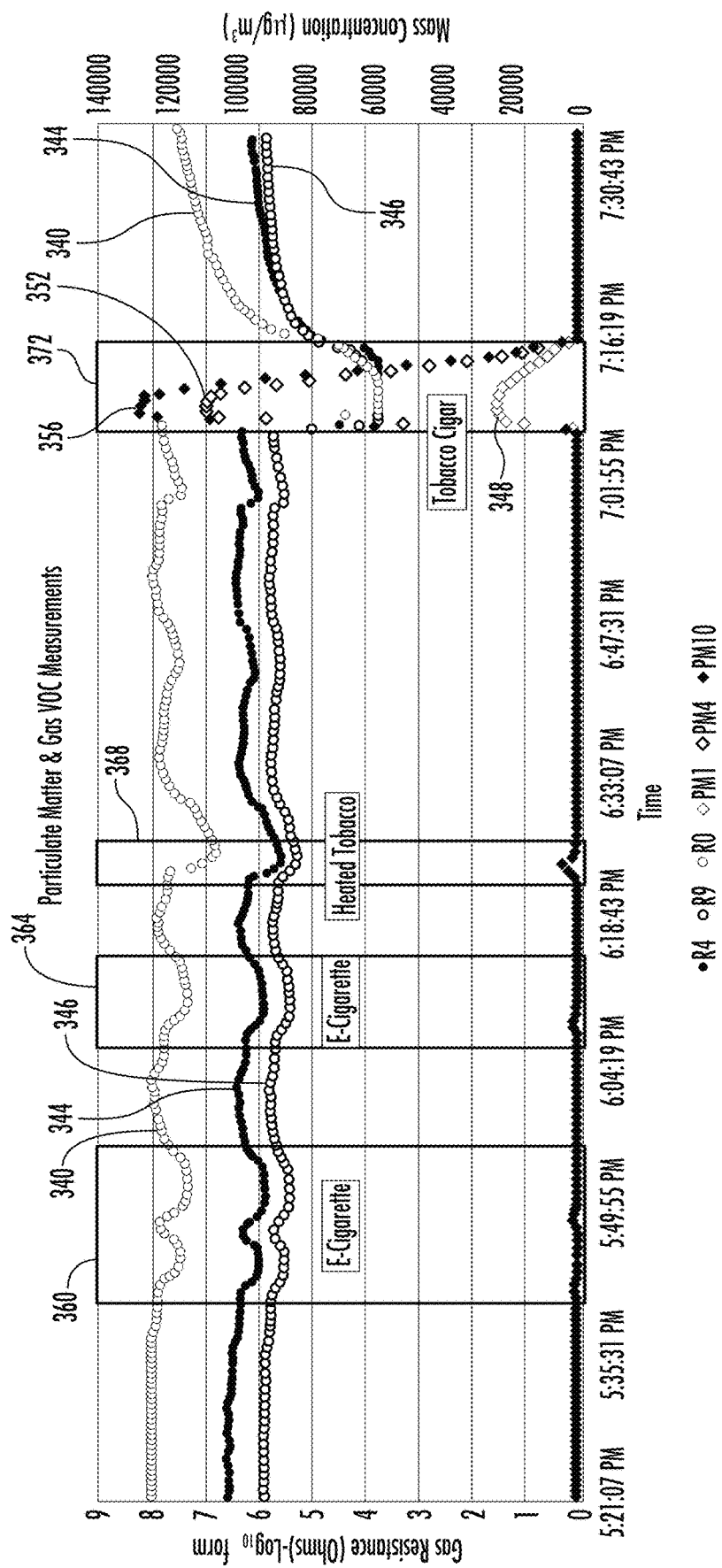
FIG. 5 shows a graph of a set of test data for a cabin event detection system such as the system of FIG. 1 highlighting certain detected events and the relationship between gas/VOC sensor data and particulate matter (PM) sensor data.
Figure 6:
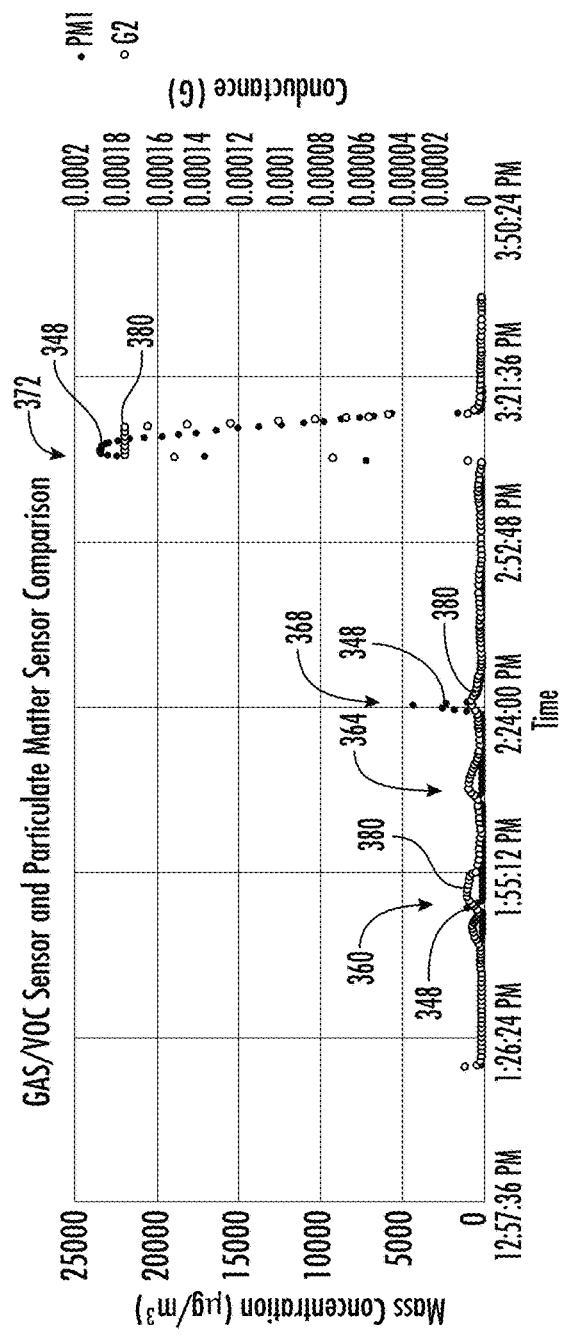
FIG. 6 shows a graph of the set of test data of FIG. 5 in which the gas/VOC sensor data is depicted as the conductance (1/R).

The relationship between PM and gas/VOC sensor data during certain classifiable events can be seen from FIGS. 5 and 6. Particularly, FIG. 5 illustrates the gas resistance readings and PM sensor data for a set of training data during known events. In particular, the gas resistance data depicts R0, R4, and R9 readings 340, 344, 346 respectively, generally at the top of the graph, along with PM1, PM4, and PM10 readings 348, 352, 356, respectively, generally at the bottom of the graph.

A brief technical overview of the sensor operation is helpful in explaining how the gas/VOC sensors and PM sensors complement each other's detection/classification abilities. First, as the gas/VOC sensor is exposed to VOCs, for example in the form of particular gases or smoke (such as cigarette smoke), a heated filament of the gas/VOC sensor used for measuring within the metal-oxide sensor (MOx) causes the organic gases to chemically react to form $CO_2$ and $H_2O$. This chemical reaction consumes oxygen, which is measured by the sensor to determine whether a particular concentration of gas(es) is near the sensor. The reduced oxygen is sensed as a drop in resistance on the semiconductor responsible for measuring the gas signal. Therefore, as oxygen near the sensor decreases, gas resistance decreases as a result. This observed decrease in gas resistance can then be used to infer a concentration of gas(es)/VOCs nearest the gas/VOC sensor at a particular point in time.

In addition, in some embodiments, the gas/VOC sensors may be tuned to generate output resistance signals that are different depending on the particular gas(es)/VOCs present. Specifically, different chemicals and gases react differently at different temperatures in the gas/VOC sensor. Therefore, as the temperature of the heated filament increases and decreases, different elements react off at different points along the scan cycle. Accordingly, the gas/VOC sensor generates different sensor resistance readings in the metal oxide sensing element at different temperatures, and these different readings are output as different sensor resistance signals.

Figure 7:
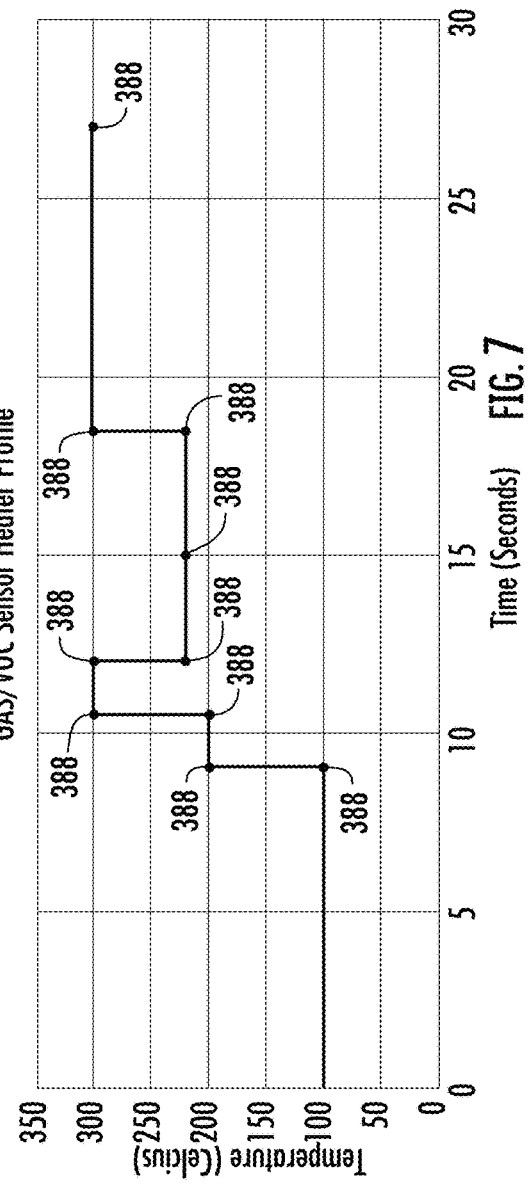
FIG. 7 is a graph showing the temperature over time and the temperature registers for a temperature of one particular gas/VOC sensor.

FIG. 7 illustrates one example of a gas/VOC sensor heater profile during a scan cycle. As seen in FIG. 7, the sensor is programmed such that the temperature increases and decreases in several steps over the span of approximately 27 seconds. At each of the ten registers 388 on the profile, the sensor generates a sensor reading, for example, identified as readings R0 to R9. Because different gases respond differently to the different temperature steps, the readings R0 to R9 reflect the presence of different gas signatures. Moreover, in some embodiments, the temperature profile (i.e. the temperature steps, times, and register timing) is tuned based on the particular set of gases so as to enable the system 104 to identify a desired set of gases. For example, a specific gas, or combination of gases, can be analyzed at different heater profiles to develop a "fingerprint" of the particular gas or gases. The learned parameters associated with the gas fingerprint can be used to modify the heater profile sequence so as to enable the gas/VOC sensor to target the particular gas or combination of gases. As a result, the gas/VOC sensor can be tuned to target the gas or gases most relevant to the event determination by the cabin event detection system 104.

In FIG. 5, three resistance signals, R0 340, R4 344, and R9 346, are generated. In some embodiments, the sensors may be calibrated to generate up to 16 different resistance signals at any given time that are based on different gases and chemicals in the sensed air. The various different resistance profiles enable specific calibration of the gas/VOC sensors to provide additional data that form part of the corpus of training data, and this further data enables the disclosed cabin event detection system 104 to classify a variety of different events occurring in the cabin 108 of the vehicle 100 based on the different gas resistance profiles. By way of example, the gas/VOC sensor may be calibrated to identify ethanol in the air indicative of alcohol on a user's breath, combustion products indicative of smoke, chemical compounds or VOCs indicative of vaping exhalation (e.g. nicotine, solvents, tobacco byproducts, hydrocarbons, flavorings, etc.), chemical compounds indicative of drug use, or organic compounds indicative of the presence of food, objectionable smells, or vomit.

Referring back to FIG. 5, it can be seen that in the first vape event 360, the gas resistance signals 340, 344, 346 from the gas/VOC sensor drops twice, while the PM readings experience two slight increases at the beginning of each reduction in gas resistance. These signals are evidence of a passenger in the cabin 108 exhaling twice from a vaping device in quick succession. After the initial rises in PM concentrations, the concentration begins to settle as smoke decays and the detected PM values 348, 352, 356 begin to lower back down to previous background conditions. Similarly, as the vapor in the air decays, the gas/VOC sensor is exposed to more oxygen and as a result the gas resistance signals 340, 344, 346 recorded from the gas/VOC sensor begins to rise. A comparable signature is evident in the second vape event 364, with the PM readings 348, 352, 356 increasing slightly at the beginning of a reduction in the gas resistance signals 340, 344, 346 and the sensor signals 340-356 returning to background values as the vapor in the air decays.

The machine learning model stored in the controller 112 is configured to identify the occurrence of an event and classify the event as a vaping event based on the trained signature of the vaping event, which is, for example, a relatively short duration and relatively slight increase in PM concentrations 348, 352, 356 and a longer duration reduction in the gas resistance readings 340, 344, 346.

A heated tobacco event 368 is also depicted in FIG. 5. In the heated tobacco event 368, the gas resistance readings 340, 344m 346 decrease, with the R0 readings 340 in particular exhibiting a sharp decrease with a relatively fast recovery. The PM sensor readings 348, 352, 356 increase to a greater degree than in the vaping events 360, 364, and also exhibit a relatively short duration increase followed by a short duration recovery.

The sensor data signatures of the vaping and heated tobacco events 360, 364, 368 can be contrasted to the signature of the cigar event 372 shown in FIG. 5. In the detected cigar event, the PM sensor signals 348, 352, 356, particularly the PM10 signal 356 and the PM4 signal 352, exhibit a large increase, while the gas sensor resistances 340, 344, 346 drop precipitously and remain at the lower limit of the sensor for approximately 20 seconds.

FIG. 6 illustrates the same four events 360-372 as in FIG. 5, but with only PM1 readings 348 and one gas conductance (1/R) reading 380 shown. As seen in FIG. 6, the gas conductance 380 is correlated with the PM1 signal 348 for all of the detected events 360-372. Based on the relationship between the PM sensor reading(s) and the gas conductance or resistance reading(s), the machine learning model develops learned parameters, kernel weights, filter values, mathematical functions, etc. for which certain patterns of sensor data are classified as detected types of events.

A quick comparison between the gas/VOC and PM sensor signals evidences how both sensor signals complement one another. Specifically, for vaping, heated tobacco, and smoking events, the event is detected by both sensors. As a result, the sensor data from both the PM and gas/VOC sensors provide enhanced confidence in a detected event, but also additional data that can be used to classify the specific event detected.

Moreover, the gas/VOC sensors offer the capability of identifying gases and VOCs in a given environment based on data that is unavailable from PM sensors alone. For example, consuming or possessing open alcohol containers and exhaling alcohol from a user's breath generally do not cause an increase in particulate matter in the cabin of the vehicle. However, the alcohol results in gases and VOCs being present in the air in the cabin, and these gases and VOCs are detectable by the gas/VOC sensors. As a result, the presence of alcohol in the vehicle, either in open containers or on the breath of one or more occupants, can be classified based on the presence of a certain signature of the gas/VOC sensor readings in combination with a minimal or no appreciable increase in detected particulate matter.

Figure 8:
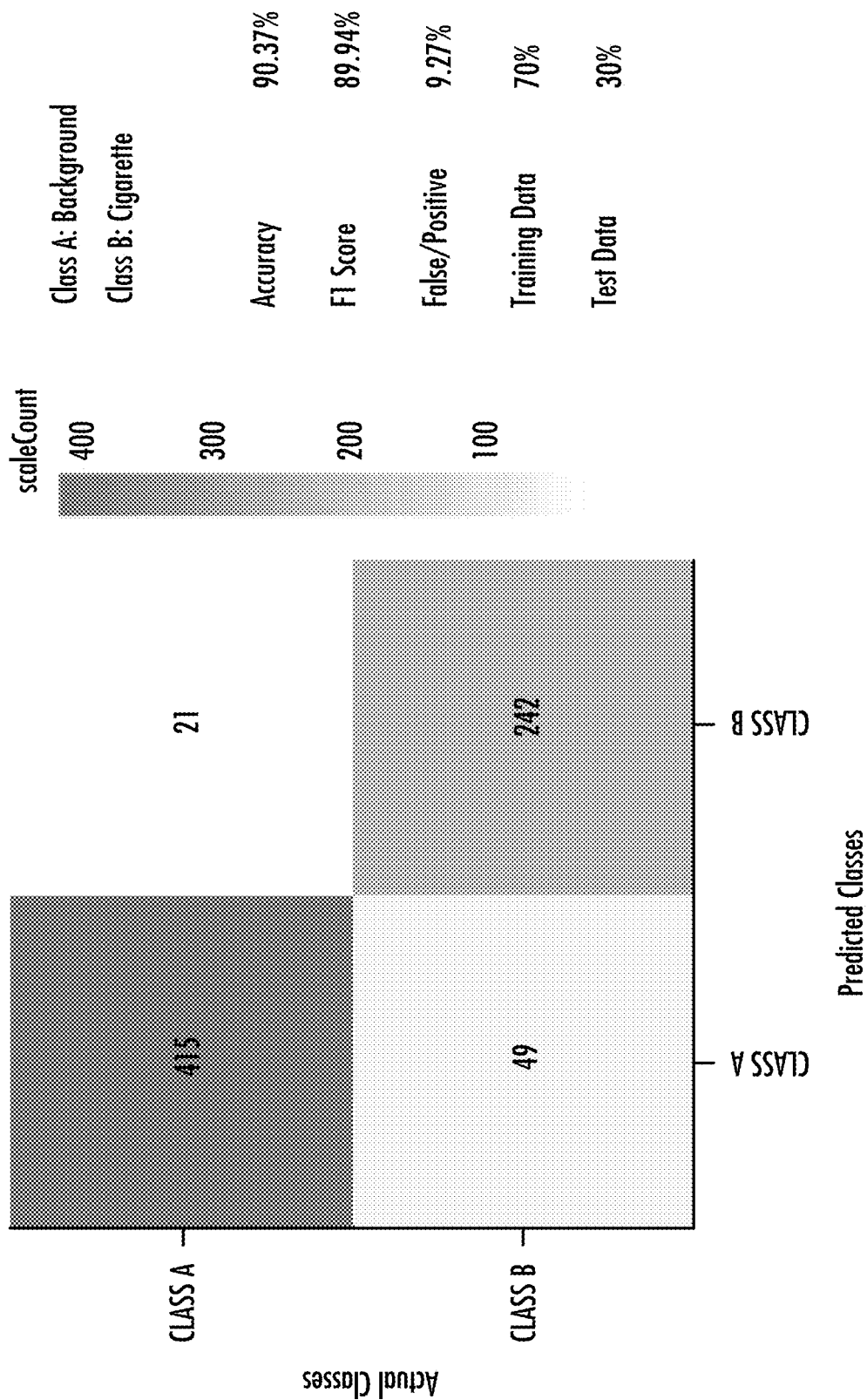
FIG. 8 illustrates a confusion matrix for a set of test data used in a cabin event detection system such as the system of FIG. 1.

FIG. 8 depicts a confusion matrix generated as a result of using the machine learning model trained as described above with test and training PM and gas/VOC sensor data for distinguishing between background and cigarette smoking data. As can be seen, in the testing model, the machine learning model disclosed herein provides accuracy on the order of 90%, which is an improvement over PM detection systems along. Moreover, over time, the corpus of training data increases, thereby increasing the accuracy of the machine learning model over time.

Event Determination with One or More Image Sensors

Figure 9:
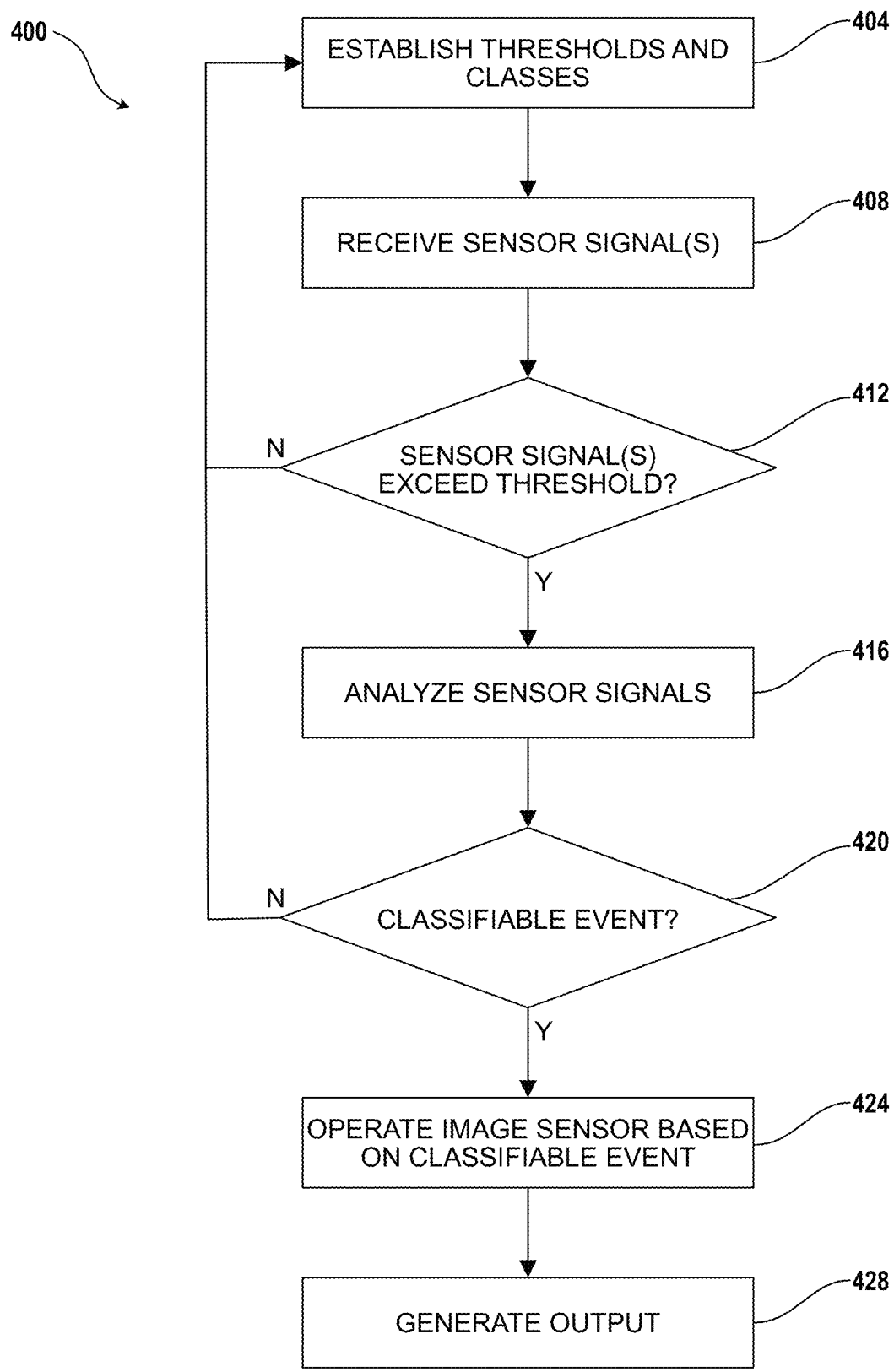
FIG. 9 is a process diagram illustrating a method of operating the cabin event detection system of FIG. 1 that includes an image sensor.

FIG. 9 depicts another method 400 for determining an event in the cabin 108 of the vehicle. In the method of FIG. 9, the cabin event detection system 104 includes at least one image sensor 132, which is operated according to the method 400 during the event detection and classification. The method 400 is executed at least in part by the controller 112 executing program instructions stored in the memory 136 to detect and determine an event in the cabin 108.

The method 400 begins with establishing one or more threshold values and event classes (block 404). The threshold values are established in the same manner as in block 204 described above in the method 200. In some embodiments, the classes are also established in the same manner as in block 204. Alternatively, the training data used to establish the classes in block 408 may also include image sensor training data.

More specifically, the cabin event detection system 104 establishes the event classifications based on training data and previously received sensor data, collectively referred to as the data. The training data may include PM data, gas/VOC data, and image sensor data for various known classification events. For example, the training data may include the corresponding PM, gas/VOC, and image sensor data for a plurality of known vaping, IQOS, cigar, cigarette, vomit, alcohol, perfume, marijuana, drug, food, pet, etc. events. In particular, the training data is based on time series datasets of the known events for the PM sensor readings, gas/VOC sensor readings, and the image sensor readings.

The machine learning or statistical model is configured to abstract the sensor data such that it is easier for the cabin event detection system 104 to process. Any machine learning or statistical models can be adopted for this purpose, such as clustering (e.g., mean shift, k-means), function approximation (e.g., Gaussian mixture model, neural networks), or simple statistical analysis (e.g., mean and deviation, histogram). In some embodiments, the model(s) may comprise machine learning models such as nearest neighbor, naive Bayes, decision trees, linear regression, neural networks (including convolution neural networks, recurrent neural networks, or artificial neural networks), or the like.

The machine learning model may apply more than one of the aforementioned learning or statistical models. For example, the PM and gas/VOC sensor data may be analyzed by one machine learning model, and the classifications for the image sensor analysis may be based on a different machine learning model. Alternatively, the image sensor analysis may be performed independently but by the same type of machine learning model as the PM and gas/VOC sensor analysis. In still other embodiments, the image sensor analysis is part of the same machine learning model as the PM and gas/VOC sensor analysis.

The training data for the image sensor 132 is based on features identified in some or all of the pixels, or groups of pixels. For instance, the training data may include images of known smoking or vaping events that are associated with the corresponding image data. The machine learning model learns the relationship and/or correlation between certain pixels or groups of pixels indicative of smoke or vapor present in the cabin 108. In some embodiments, the training data may include image data corresponding to known containers of alcohol, for example beer bottles or cans, wine bottles, or liquor bottles, or known containers of food or other drinks to train the machine learning model to identify food or beverage containers in the vehicle. Additionally or alternatively, the training data includes image data corresponding to presence of pets or other animals to train the machine learning model to identify the presence of pets or animals in the cabin 108.

Once the thresholds and classes are established in block 404, the method 400 proceeds with receiving one or more sensor signals from at least one of the sensors 116, 120 (block 408), and determining whether the sensor signal(s) exceed the established threshold (block 412). These steps are performed in the same manner described above with reference to the steps 208, 212 of the method 200, and are not described in further detail here.

The method then proceeds with analyzing the sensor signals (block 416) and determining whether a classifiable event has occurred (block 420). In one embodiment, the analysis of the sensor signals and the determination of the classifiable event are performed in the same or substantially the same manner as the analysis and determination of the classifiable event of the method 200. In other words, time series datasets are generated of the PM sensor data and the gas/VOC sensor data, and the machine learning model established from the training data analyzes the time series datasets.

In another embodiment, the image data is incorporated into the analysis of the sensor signals and the determination of the classifiable event. In particular, the controller 112 is configured to analyze the image data from the one or more image sensors using either the same machine learning model that analyzes the PM and gas/VOC sensor data or a different machine learning model to identify the classifiable event. The analysis of the image sensor data may be based on a single image, a series of images, or a video captured by the image sensor 132.

As in the method 200, the analysis of the sensor signals at block 416 and the determination of whether a classifiable event has occurred at block 420 are performed by the controller 112 by a processor located in or on the vehicle 100 or by a processor located remotely, for example in the cloud backend 160.

If, in block 420, the received sensor signals from both the PM sensors 116 and the gas/VOC sensors 120, and in some embodiments the image sensor 132, are classified by the machine learning model as one of the events learned in the training process, the method proceeds to operate the image sensor based on the classifiable event (block 424). Particularly, the controller 112 generates at least one control signal to operate the image sensor 132, or a plurality of image sensors 132 in the cabin 108, to capture at least one image in the cabin 108 of the vehicle 100. The at least one image may be a single image generated by one image sensor, a single image generated by each of a plurality of image sensors so as to provide a more comprehensive view of the cabin 108, or a series or images or a video captured by one or more image sensors in the cabin. The image sensor 132 may be in the form of a plurality of cameras to provide sufficient coverage of the cabin 108 to identify each individual involved in the classified event.

In some embodiments, the controller 112 is configured to confirm the event classified in block 420 by analyzing the at least one image using a machine learning model. For example, if the controller 112 determines that a smoking event has occurred in block 420, the controller 112 may analyze the at least one image using the machine learning model to determine whether the smoking event can be confirmed. Similarly, the controller may analyze the image using the machine learning model to identify food or beverage containers, or pets or animals, if such events are determined based on the classification using the PM and gas/VOC sensor data.

Once the controller 112 has operated the image sensor(s) to capture one or more images of the cabin 108, the controller 112 proceeds to generate an output 428. The output of the controller may include any or all of the outputs discussed above with regard to block 224 of the method 200. Additionally, the output generated by the controller includes storing or transmitting the captured image data with the PM and gas/VOC sensor data in any of the aforementioned outputs, for example in the manner discussed above with regard to block 228.

For instance, the cabin event detection system 104 may be configured to notify the user and/or operator of a rule or policy violation based on the detected event. The controller 112 may transmit a notification to the user's cellular phone or ride-sharing app via cellular telephony, or via the cloud backend 160 or the third-party backend 168 that includes at least one or more of the captured images as evidence of the rule or policy violation.

In another embodiment, the controller 112 is configured to notify the operator of the vehicle of the detected event. For instance, the controller 112 may transmit a notification via, for example, email, SMS, an API connection, or a dedicated user interface (i.e. operator dashboard), to the operator of the vehicle. The notification may include data corresponding to a timestamp of the detected event, a vehicle ID, the event metadata, which may include the raw data from the datasets and/or the datasets presented in a visual manner, i.e. a graphical manner, as evidence of the detected event. Additionally, the data transmitted to the operator includes one or more of the captured images or videos provided to the operator as graphical evidence of the determined event.

In some embodiments, the output data is stored on the memory 136 or another memory either locally in the vehicle or remotely from the vehicle. Particularly, the time series datasets of the PM data and the gas/VOC data and the at least one captured image may be transmitted to the cloud backend 160 and/or the third-party backend 168, where the datasets and the capture image(s) are associated with the user's account and/or the vehicle 100. The image data may be subsequently accessed by a computer program, for example a machine learning model, or by the operator to confirm the event detected by the cabin event detection system 104, or to reject or reclassify the detected event.

Confirmation of the detected event using the image data increases the availability of confirmed training data for different classifications. For instance, based on the verification using the image data, the corresponding PM and gas/VOC data can be added to the training data as a confirmed event, thereby enabling the machine learning model to improve the classification algorithm over time.

Additionally or alternatively, the image may be transmitted along with the notification sent to the user as further evidence of the detected event. The image may, for example, be used as supporting evidence in the event the user disputes the characterization of the classified event as a violation of the rules or policies. Alternatively, the image may be stored in the memory 136 to support the assignment of cleaning charges to one or more passengers in the cabin 108.

It is possible that in some scenarios a single image obtained after a classifiable event has been identified will not reveal which individual within the vehicle was involved in the classifiable event since events such as smoking, vaping, and alcohol consumption are intermittent events. Accordingly, in some embodiments the image sensor 132 is controlled by the controller 112 to obtain images in a continuous loop. Thus, the operation of the image sensor at block 424 may cause a video clip or series of images taken from before the classified event was identified up to and/or beyond the time that the classified event was identified to be stored in the memory 136 and/or transmitted to a remote location such as one of the cloud backends 160, 168. In one or more embodiments, the operation causes a video clip or series of images taken from at least thirty seconds before the classifiable event was identified up to the time that the classifiable event was identified to be stored. In one or more embodiments the images are obtained at a rate of two frames per second to reduce the amount of storage needed.

The disclosed cabin event detection system 104 provides a robust mechanism for determining events in the cabin 108 of the vehicle 100. Specifically, because both the PM sensors and the gas/VOC sensors are used in the determination, the system has data that is not be available to conventional smoking detection systems enabling a more robust detection and classification of more types of events. Further, the disclosed system is designed to reduce the power, processing capacity, and data transmission required since the majority of the data is not captured, analyzed, or transmitted continuously, and the data from all of the sensors is analyzed only after the threshold value has been exceeded indicating that a potentially classifiable event has occurred. Moreover, in embodiments including the image sensor, the image data associated with a classifiable event provides additional evidence for confirmation and dispute resolution related to the classifiable event.

Moreover, the data and metadata from the determined event enables operators of shared vehicle services to better maintain the shared vehicles by, for example, establishing more efficient cleaning and maintenance schedules. As a result, the operator can provide a better customer experience for users of the shared vehicles, while reducing costs associated with cleaning and maintaining vehicles when no service is necessary.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

What is claimed is:

1. A system for determining an event in a cabin of a vehicle, the system comprising:
   a gas sensor configured to generate a first sensor signal associated with a quantity of at least one gas or volatile organic compound (VOCs) in ambient air of the cabin;
   a particulate matter (PM) sensor configured to generate a second sensor signal associated with a quantity of particulate matter in the ambient air of the cabin;
   an image sensor configured to generate an image signal corresponding to a captured image of at least a portion of the cabin of the vehicle; and
   a controller operably connected to the gas sensor, the PM sensor, and the image sensor and configured to:
      receive the first and second sensor signals from the gas sensor and the PM sensor;
      generate a first time series dataset of the first sensor signals and a corresponding second time series dataset of the second sensor signals;

determine an event in the cabin of the vehicle by analyzing both the first and second time series datasets using a machine learning model that has been trained with training data corresponding to time series data of PM readings and gas sensor readings of known events; and in response to determining the event in the cabin, operate the image sensor to generate image data corresponding to a captured image of at least a portion of the cabin of the vehicle.

2. The system of claim 1, wherein the controller is further configured to notify an operator of the vehicle of the determined event.

3. The system of claim 2, wherein the notifying of the operator of the vehicle includes transmitting to the operator the captured image of at least the portion of the cabin of the vehicle.

4. The system of claim 3, wherein the notifying of the operator further includes transmitting to the operator at least part of the first and second time series datasets associated with the determined event.

5. The system of claim 1, further comprising:
a memory operably connected to the controller,
wherein the controller is further configured to store at least part of the first and second time series datasets and the image of at least the portion of the cabin of the vehicle in the memory in such a way that the at least part of the first and second time series datasets and the image are associated with the determined event.

6. The system of claim 1, wherein:
the machine learning model or a further machine learning model has been trained is with training data corresponding to captured images of the known events, and
the controller is further configured to confirm the determined event by using the machine learning model or the further machine learning model to analyze the image of the at least the portion of the cabin of the vehicle.

7. The system of claim 1, wherein the machine learning model is an artificial neural network.

8. The system of claim 1, wherein the controller is further configured to:
compare one of the first sensor signal and the second sensor signal with a threshold value before generating the first and second time series datasets, and
generate the first and second time series datasets and determine the event in the cabin in response to the one of the first sensor signal and the second sensor signal exceeding the threshold value.

9. The system of claim 8, wherein:
the controller includes at least one local processor disposed in the vehicle and at least one remote processor disposed remote from the vehicle and in wireless communication with the at least one local processor,
the at least one local processor is configured to compare the one of the first sensor signal and the second sensor signal with the threshold value, and
the at least one remote processor is configured to determine the event in the cabin of the vehicle.

10. The system of claim 1, wherein the controller is further configured to update the training data to include the first and second datasets in response to determining the event.

11. A method for determining an event in a cabin of a vehicle, the method comprising:
receiving, with a controller, a first sensor signal from a gas sensor configured to generate the first sensor signal, which is associated with a quantity of at least one gas or volatile organic compound (VOC) in ambient air of the cabin;
receiving, with the controller, a second sensor signal from a particulate matter (PM) sensor configured to generate the second signal, which is associated with a quantity of particulate matter in the ambient air of the cabin;
generating, with the controller, a first time series dataset of the first sensor signals and a corresponding second time series dataset of the second sensor signals;
determining, with the controller, an event in the cabin of the vehicle by analyzing both the first and second time series datasets using a machine learning model that has been trained with training data corresponding to time series data of PM readings and gas sensor readings of known events; and
in response to determining the event in the cabin, operating an image sensor to generate image data corresponding to a captured image of at least a portion of the cabin of the vehicle.

12. The method of claim 11, further comprising:
notifying an operator of the vehicle of the determined event.

13. The method of claim 12, wherein the notifying of the operator of the vehicle includes transmitting to the operator the captured image of at least the portion of the cabin of the vehicle.

14. The method of claim 13, wherein the notifying of the operator further includes transmitting to the operator at least part of the first and second time series datasets associated with the determined event.

15. The method of claim 11, further comprising:
storing, in a memory that is operably connected to the controller, at least part of the first and second time series datasets and the image of at least the portion of the cabin of the vehicle in such a way that the at least part of the first and second time series datasets and the image are associated with the determined event.

16. The method of claim 11, further comprising:
confirming the determined event by using the machine learning model or the further machine learning model, which has been trained with training data corresponding to captured images of the known events, to analyze the image of the at least the portion of the cabin of the vehicle.

17. The method of claim 11, wherein the machine learning model is an artificial neural network.

18. The method of claim 11, further comprising:
comparing one of the first sensor signal and the second sensor signal with a threshold value before generating the first and second time series datasets; and
generating the first and second time series datasets and determine the event in the cabin in response to the one of the first sensor signal and the second sensor signal exceeding the threshold value.

19. The method of claim 18, wherein:
the comparing of the one of the first sensor signal and the second sensor signal with the threshold value is executed by at least one local processor of the controller that is disposed in the vehicle, and
the determining of the event in the cabin of the vehicle is executed by at least one remote processor that is disposed remote from the vehicle and is in wireless communication with the at least one local processor.

20. The method of claim 11, further comprising:

updating the training data to include the first and second datasets in response to determining the event.

* * * * *

UNITED STATES PATENT AND TRADEMARK OFFICE
CERTIFICATE OF CORRECTION

PATENT NO. : 12,260,652 B2
APPLICATION NO. : 18/173222
DATED : March 25, 2025
INVENTOR(S) : Brohl et al.

Page 1 of 1

It is certified that error appears in the above-identified patent and that said Letters Patent is hereby corrected as shown below:

In the Claims

In Claim 6, at Column 19, Line 32: "has been trained is with training data" should read --has been trained with training data--.

Signed and Sealed this
First Day of July, 2025

Coke Morgan Stewart
*Acting Director of the United States Patent and Trademark Office*